United States Patent [19]
Stevens

[11] Patent Number: 5,628,671
[45] Date of Patent: May 13, 1997

[54] OBSERVATION HIVE

[76] Inventor: John A. Stevens, 238 Kennedy Ave., Schererville, Ind. 46375

[21] Appl. No.: 417,789

[22] Filed: Apr. 6, 1995

[51] Int. Cl.⁶ .................................................. A01K 47/06
[52] U.S. Cl. .................. 449/6; 449/14; 449/37
[58] Field of Search ................... 449/6, 11, 13, 449/14, 37

[56] References Cited

U.S. PATENT DOCUMENTS

| | | |
|---|---|---|
| Re. 22,044 | 3/1942 | O'Beirne. |
| 181,753 | 8/1876 | Wiley. |
| 519,652 | 5/1894 | Taylor ................................. 449/37 X |
| 736,226 | 8/1903 | Danzenbaker. |
| 1,048,950 | 12/1912 | Danzenbaker. |
| 1,211,587 | 1/1917 | Jordan. |
| 2,103,066 | 12/1937 | Engelbrektsson. |
| 2,150,067 | 3/1939 | Kelley. |
| 2,326,250 | 8/1943 | O'Beirne. |
| 2,717,432 | 9/1955 | Willard. |
| 3,071,784 | 1/1963 | Kolb. |
| 3,088,134 | 5/1963 | Abel. |
| 3,088,135 | 5/1963 | Covington. |
| 3,806,969 | 4/1974 | Varama. |
| 4,094,026 | 6/1978 | Simoni. |
| 4,263,684 | 4/1981 | Stevens. |
| 4,483,031 | 11/1984 | Shaparew ................................ 449/14 |

Primary Examiner—Robert P. Swiatek
Attorney, Agent, or Firm—Emrich & Dithmar

[57] ABSTRACT

An observation hive includes a main frame including bottom and side frame members and glass front and rear walls which cooperate to define an open-top chamber in which two honeycomb frames are removably mounted. Front and rear top frame members interconnect the upper ends of the side frame members and respectively seat against the outer surfaces of the glass walls. A cover overlies the top and side frame members to close the chamber and has a depending insert portion which substantially completely occupies the portion of the chamber extending above the bottom edges of the top frame members so that bees cannot enter this space and be unobserved. Ventilation holes are formed vertically through the cover and the bottom frame member to allow vertical flow of air through the chamber, each ventilation opening being screened at its upper and lower ends. The bottom frame member is seated on pedestals to provide a clearance space therebeneath. The honeycomb frames are suspended on spacer blocks which are slidably received in dovetail-shaped grooves in the side frame members, each spacer block having a laterally extending spacer pin to laterally position the honeycomb frames. In an alternative embodiment, the ventilation openings in the bottom frame member are formed in a removable section, which facilitates access to the bottom of the chamber.

19 Claims, 2 Drawing Sheets

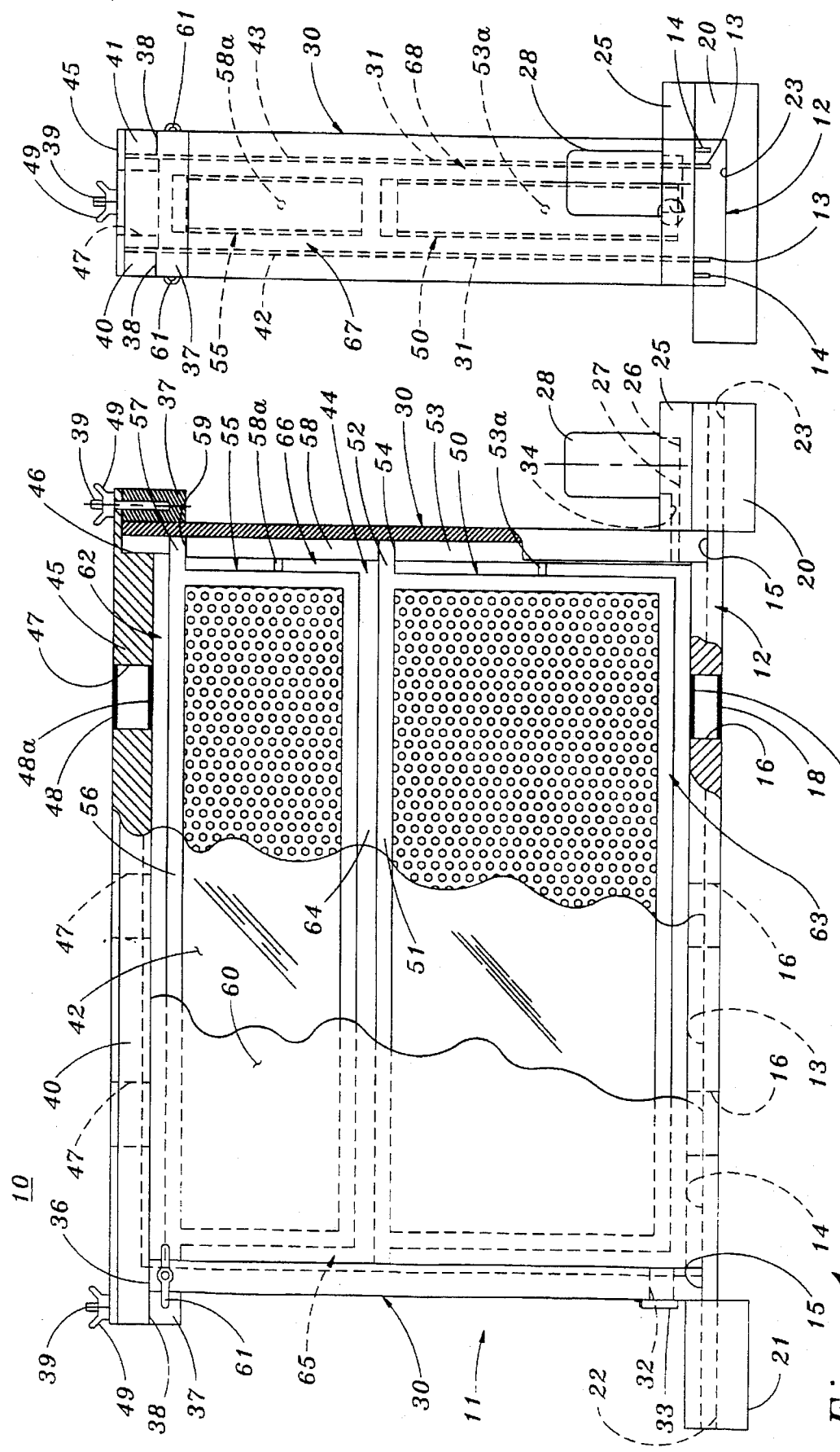

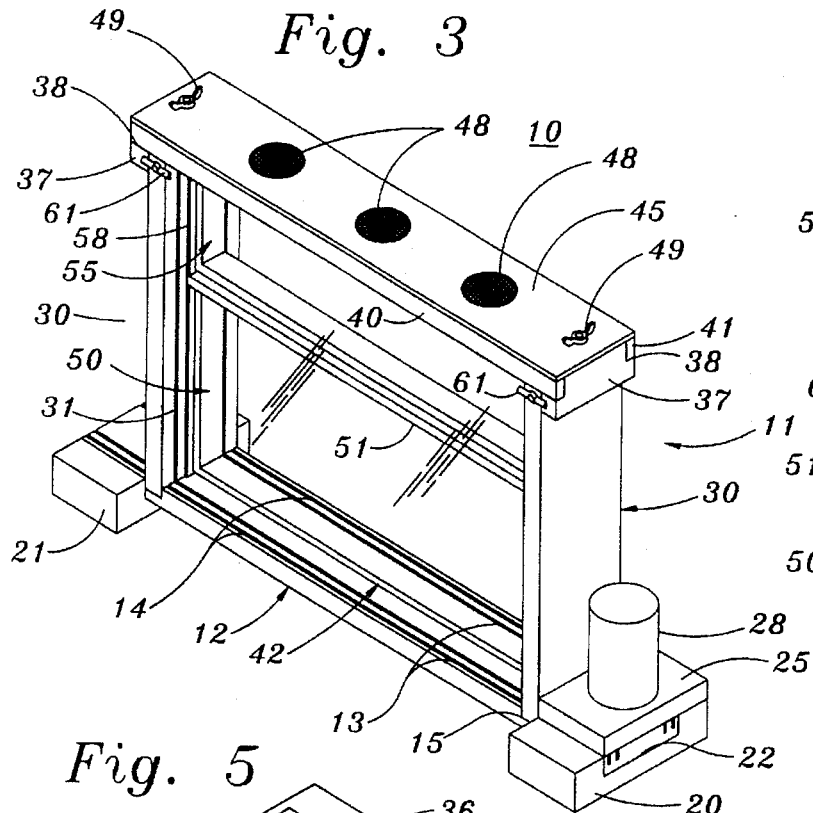
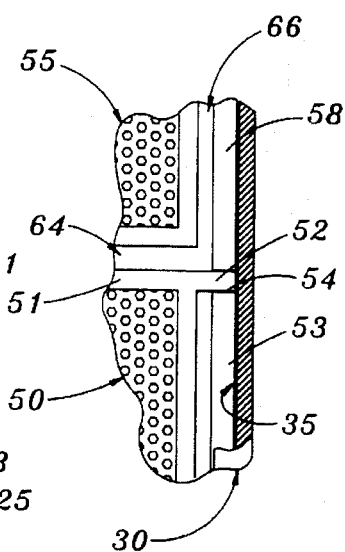
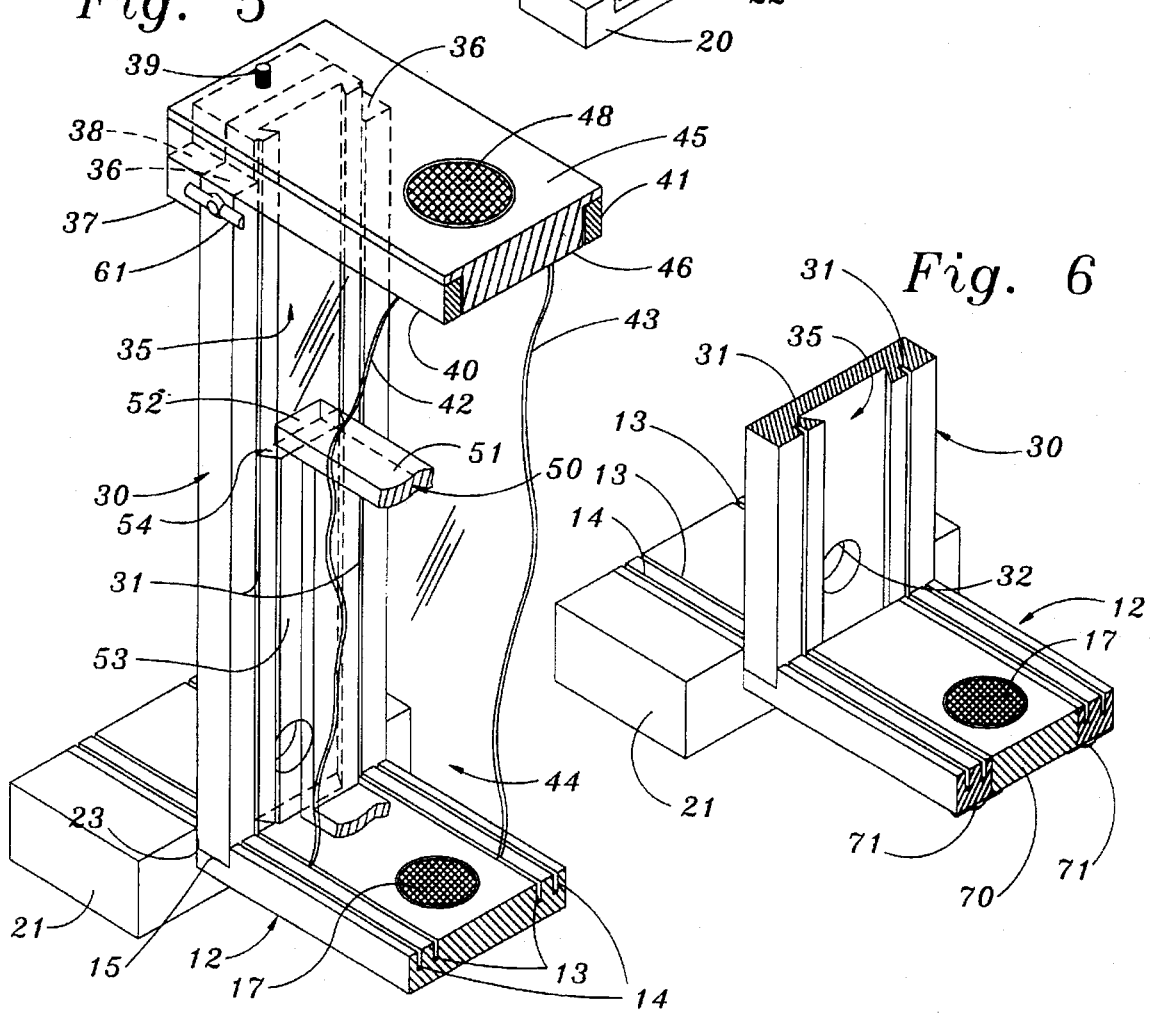
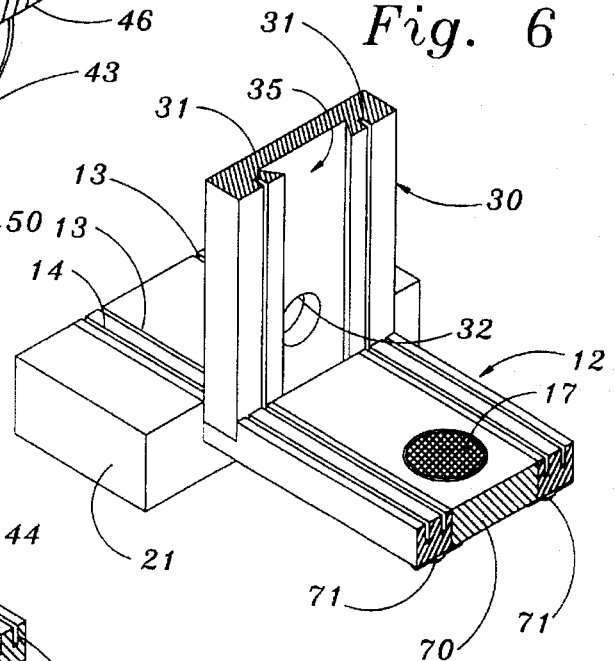

5,628,671

OBSERVATION HIVE

BACKGROUND OF THE INVENTION

1. Field of the Invention

The present invention relates to observation beehives.

2. Description of the Prior Art

This invention is an improvement of the observation hive disclosed in applicant's U.S. Pat. No. 4,263,684, the disclosure of which is incorporated herein by reference. That observation hive comprises a main frame including a horizontal bottom frame member and two upstanding side frame members and front and rear top frame rails interconnecting the tops of the side frame members at the front and rear edges thereof. Spaced-apart front and rear transparent walls are, respectively, mounted in the main frame against the inner surfaces of the top frame members and cooperate with the bottom and side frame members to define an open-top rectangular chamber which removably receives two honeycomb frames.

The honeycomb frames are supported on, and are vertically spaced apart by, spacer blocks which are mateably slidably received in longitudinal dovetail-shaped channels or grooves formed on the inner surfaces of the side frame members. More specifically, there are two pairs of spacer blocks, a bottom pair seats in the lower ends of the dovetail-shaped channels and have upper ends which define support surfaces for receiving projecting support arms which, respectively, project laterally from the top of the lower honeycomb frame. The upper pair of spacer blocks are, respectively, received on top of the support arms and define upper support surfaces which receive support arms of the upper honeycomb frame. The parts are so dimensioned and arranged that, when thus mounted in place, the lower honeycomb frame will be vertically spaced a "bee space" distance from the bottom frame member and the upper honeycomb frame will be vertically spaced that distance above the lower honeycomb frame member. Similarly, the honeycomb frames are dimensioned such that they will be spaced the "bee space" distance from the transparent walls and from the side frame members, the "bee space" distance falling within a predetermined range.

A cover closes the top of the chamber and includes a spacer block which bears against the top of the upper honeycomb frame to clamp it in place. A feeder opening is provided in the cover and vent openings are provided in each of the side frame members. Opaque shield panels may be mounted in place over the outside of each of the transparent walls to protect them in transit and/or to shield the hive from ambient light.

While this prior art beehive is generally effective, it has a number of disadvantages. The chamber in which the honeycomb frames are mounted extends up to the level of the top surfaces of the front and rear top frame members. Since these top frame members have a vertical thickness of at least the size of a bee, bees could move into the upper end of the chamber behind the top frame members and avoid observation by the user. Also, the side-mounted vent holes do not provide optimal ventilating air flow throughout the chamber. More specifically, the air flow is insufficient to adequately eliminate moisture from the chamber. Furthermore, this side ventilation arrangement necessitates that vent holes also be formed through the spacer blocks.

Most parts of the hive are preferably formed of wood. They are not precision dimensioned and are subject to expansion and contraction with changes in temperature, humidity and the like. Thus, the parts are made with enough clearance to accommodate these dimensional changes. This can allow some lateral shifting of the honeycomb frames which might be sufficient to alter the bee space distances on the opposite ends of the honeycomb frames so that they fall outside the predetermined range. Also, access to the chamber can be had only through the top by opening the cover.

SUMMARY OF THE INVENTION

It is a general object of the invention to provide an improved observation hive which avoids the disadvantages of prior hives while affording additional structural and operating advantages.

An important feature of the invention is the provision of an observation hive which affords improved ventilation sufficient to adequately eliminate moisture from the hive.

In connection with the foregoing feature, a further feature of the invention is the provision of an observation hive of the type set forth, which accommodates vertical air flow throughout the entire vertical height of the hive chamber.

A further feature of the invention is the provision of an observation hive of the type set forth, which affords no spaces for bees to move out of sight of the observer.

Yet another feature of the invention is the provision of an observation hive of the type set forth which accurately maintains bee spaces around the honeycomb frames.

Yet another feature of the invention is the provision of an observation hive of the type set forth which is of relatively simple and economical construction.

These and other features of the invention are attained by providing an observation hive for honey bees and the like comprising: a main frame including a bottom frame member and two opposed side frame members and spaced-apart front and rear top frame members, spaced-apart front and rear walls disposed within the main frame respectively against the front and rear top frame members and cooperating with the bottom and side frame members to define an open-top chamber, at least one of the walls being transparent, a removable cover overlying the side and top frame members for closing the chamber, a honeycomb frame removably mounted in the chamber and spaced from the bottom frame member and from the cover and from the walls, the bottom frame member and the cover having ventilation openings formed vertically therethrough and communicating with the chamber to accommodate air flow vertically through the chamber, support pedestals connected to the bottom frame member for establishing a clearance space therebeneath, and screens respectively covering the ventilation openings to permit passage of air and prevent passage of bees.

The cover includes an insert portion depending between the side frame members and between the top frame members and substantially completely occupying the portion of the chamber which extends above the bottom edges of the top frame members. The main frame also includes spacing structure coupled to each of the side frame members and including spacers extending laterally inwardly to engage the honeycomb frame for maintaining a predetermined minimum spacing between the honeycomb frame and the side frame members. In one embodiment a removable bottom section permits easy access to the bottom of the hive.

The invention consists of certain novel features and a combination of parts hereinafter fully described, illustrated in the accompanying drawings, and particularly pointed out in the appended claims, it being understood that various changes in the details may be made without departing from the spirit, or sacrificing any of the advantages of the present invention.

BRIEF DESCRIPTION OF THE DRAWINGS

For the purpose of facilitating an understanding of the invention, there is illustrated in the accompanying drawings a preferred embodiment thereof, from an inspection of which, when considered in connection with the following description, the invention, its construction and operation, and many of its advantages should be readily understood and appreciated.

FIG. 1 is a front elevational view of the observation hive of the present invention, with portions broken away and in partial vertical section;

FIG. 2 is a end elevational view of the observation hive of FIG. 1, as viewed from the right-hand end thereof;

FIG. 3 is a reduced front perspective view of the observation hive of FIG. 1;

FIG. 4 is a fragmentary front elevational view in vertical section of a portion of the right-hand side of the observation hive of FIG. 1;

FIG. 5 is an enlarged, fragmentary, perspective view of the left-hand end of the observation hive of FIG. 1, with the upper honeycomb frame removed therefrom more clearly to illustrate the construction; and FIG. 6 is a fragmentary perspective view similar to FIG. 5, illustrating an alternative embodiment of the present invention.

DESCRIPTION OF THE PREFERRED EMBODIMENTS

Referring to FIGS. 1–5, there is illustrated an observation hive in accordance with a first embodiment of the present invention, generally designated by the numeral 10. The observation hive 10 has a main frame 11 including a bottom frame member 12, which is an elongated rectangular member having a pair of inner grooves 13 and a pair of outer grooves 14 formed in the upper surface thereof and extending the entire length thereof. Transverse notches 15 are formed in the upper surface of the bottom frame member 12 and extend across the width thereof. Formed through the bottom frame member 12 at longitudinally space-apart locations centered between the notches 15 and between the inner grooves 13 are a plurality of circular vent openings 16. The bottom frame member 12 has a substantial thickness which may be approximately ¾ inch, and each of the vent openings 16 is provided with screens 17 and 18, respectively, at the upper and lower ends thereof (see FIG. 1).

The bottom frame member 12 is supported at its opposite ends on pedestals 20 and 21. More specifically, the ends of the bottom frame member 12 are, respectively, seated in rectangular channels 22 and 23 formed across the pedestals 20 and 21, each of the pedestals 20 and 21 projecting forwardly and rearwardly a substantial distance beyond the front and rear edges of the bottom frame member 12. Mounted on one of the pedestals 20 and 21 outboard of the adjacent notch 15 is a rectangular feeder block 25 having a feeder chamber 26 formed therein, coupled by a passage 27 to the inner side edge of the feeder block 25. A feeder bottle 28 is mounted on top of the feeder block 25 for communication with the chamber 26.

The main frame 11 also includes a pair of rectangular, upstanding, parallel side frame members 30, the lower ends of which are, respectively, seated in the notches 15 in the bottom frame member 12. Each of the side frame members 30 has formed in the inner surface thereof a pair of longitudinally extending and spaced-apart parallel grooves 31, respectively aligned with the inner grooves 13 of the bottom frame member 12. Formed through one of the side frame members 30 adjacent to the lower end thereof is a circular bee entry hole 32. Preferably a closure 33 is mounted on the outer surface of that side frame member 30 and may be pivotally movable between open and closed positions relative to the entry hole 32. Formed through the other of the side frame members 30 is a bee passage 34 which communicates with the feeder passage 27.

Also formed in the inner surface of each of the side frame members 30 between the grooves 31 is a longitudinally extending dovetail-shaped groove or channel 35. Each of the side frame members 30 has front and rear notches 36 formed at its upper end, each communicating with the adjacent one of the grooves 31. Fixedly secured by suitable means to the outer surface of each of the side frame members 30 at its upper end is a rectangular reinforcing block 37, provided with notches 38 at the front and rear edges thereof which are, respectively, aligned with the notches 36 in the side frame members 30. Threaded studs 39 respectively project upwardly from the reinforcing block 37 centrally thereof.

The main frame 11 also includes front and rear top frame members 40 and 41 which are, respectively, seated in the front and rear notches 36 and 38 in the side frame members 30 and the reinforcing blocks 37 and are fixedly secured thereto by suitable means. Transparent rectangular walls 42 and 43, formed of glass, plastic or the like are, respectively, seated in the inner grooves 13 of the bottom frame member 12 and the grooves 31 in the side frame members 30, so that the upper edges of the walls 42 and 43 respectively abut the inner surfaces of the top frame members 40 and 41. The front and rear walls 42 and 43 cooperate with the bottom frame member 12 and the side frame members 30 to define a rectangular open-top chamber 44, which is closed by a removable cover panel 45.

The cover panel 45 is a rectangular member which overlies the top frame member 41 and the upper ends of the side frame members 30 and the reinforcing blocks 37, the panel 45 having holes therethrough for respectively receiving the studs 39.

The cover panel 45 has a rectangular, depending insert portion 46 which extends downwardly into the upper end of the chamber 44 and has a bottom surface substantially coplanar with the bottom surfaces of the top frame members 40 and 41. The insert portion 46 is dimensioned so as to extend between the side frame members 30 and between the front and rear walls 42 and 43 so as to substantially completely occupy that portion of the chamber 44 which extends above the bottom edges of the top frame members 40 and 41. Formed through the cover panel 45 are longitudinally spaced-apart, circular vent openings 47 which may be vertically aligned with the vertical openings 16 in the bottom frame member 12, each of the openings 47 being closed by screens 48 and 48a, respectively, at the upper and lower ends thereof. Wing nuts 49 are threadedly engageable with the studs 39 for retaining the cover panel 45 in place.

The observation hive also includes two honeycomb frames removably mounted therein, including a standard honeycomb frame 50 and a shallow honeycomb frame 55, which are of conventional construction and may be of the type disclosed in the aforementioned U.S. Pat. No. 4,263,684. The standard honeycomb frame 50 is a rectangular frame including a horizontally extending top rail 51, which has laterally extending ends defining support arms 52 which project well beyond the adjacent sides of the frame. Mateably slidably received in the dovetail-shaped grooves 35 of the side frame members 30 are elongated spacer blocks 53, which bottom on the bottom frame member 12 and respectively define upper support surfaces 54. In use, the support arms 52 of the standard honeycomb frame 50 are, respectively, supported on the support surfaces 54, the spacer blocks 53 being so dimensioned that the honeycomb frame 50 is supported with its bottom edge spaced the bee space distance from the bottom frame member 12.

The shallow honeycomb frame member 55 similarly has a top rail 56 with laterally projecting support arms 57, which are respectively supported by a second pair of spacer blocks 58, which are received in the dovetail-shaped grooves 35 on top of the support arms 52. More specifically, the spacer blocks 58 define support surfaces 59 at their upper ends on which the support arms 57 rest. The spacer blocks 58 are so dimensioned that the thus-supported shallow honeycomb frame 55 has its bottom edge spaced the bee space distance from the top rail 51 of the standard honeycomb frame 50, and with the top rail 56 spaced the bee space distance vertically below the top frame members 40 and 41. It will also be appreciated that the honeycomb frames 50 and 55 are dimensioned so that, when supported in place in the chamber 44, their side edges are, respectively, spaced laterally inwardly the bee space distance from the associated spacer blocks 53 and 58, as can best be seen in FIG. 1.

In order to prevent any lateral shifting of the honeycomb frames 50 and 55 in the dovetail-shaped grooves 35, the spacer blocks 53 and 58 are, respectively, provided with laterally inwardly extending spacer studs 53a and 58a (two shown in FIG. 1), disposed for engagement with the adjacent side edges of the honeycomb frames 50 and 55 to maintain the requisite spacing from the side frame members 30. The studs 53a and 58a may be threadedly engaged with the spacer blocks 43 and 58 so as to be adjustable. It will, of course, also be appreciated that the honeycomb frames 50 and 55 are dimensioned so that, when mounted in place, they will be spaced the bee space distance from the front and rear observation walls 42 and 43.

The observation hive 10 may also be provided with a pair of rectangular shield panels 60 (see FIG. 1), which are dimensioned to respectively completely cover the exposed outer surfaces of the observation walls 42 and 43, the shield panels 60 preferably respectively having lower edges which are receivable in the outer grooves 14 in the bottom frame member 12. The shield panels 60 may be retained in place by wing nuts 61 on the side frame members 30. It will be appreciated that these shield panels 60 serve to protect the observation walls 42 and 43 when the hive 10 is in transit and also serve to shield the chamber 44 from ambient light when the hive activity is not being observed.

The observation hive 10 affords a number of significant advantages. Because the bottom edges of the top frame members 40 and 41 and the dependent insert portion 46 of the cover panel 45 are substantially coplanar, there are no areas of the chamber 44 into which bees can move beyond the view of the observer. The support of the bottom frame member 12 on the pedestals 20 and 21 provides a clearance or air space beneath the bottom frame member 12 which, together with the vent openings 16 and 47, accommodate a vertical flow of air completely through the chamber 44. This has been found to be effective to provide adequate ventilation sufficient to remove moisture from the chamber 44. The screening at both the upper and lower ends of each of the vent openings 16 and 47 prevents bees from entering those openings and prevents a user's fingers from entering the openings, thereby protecting the user from accidental stings.

The spacer studs 53a and 58a serve to accurately laterally position the honeycomb frames 50 and 55 to maintain the desired bee spaces. The extension of the pedestals 20 and 21 fore and aft well beyond the front and rear edges of the bottom frame member 12 provide great stability for the hive 10, inhibiting forward or rearward tipping thereof. It will be appreciated that, for feeding, bees traverse the feeder passage 27 into the chamber 26 for access to the feeder bottle 28, in a known manner.

In observation hives, bees, which may have a life span of about two weeks, are continually dying and being replaced, with dead bees falling to the bottom of the chamber 44 and collecting on the bottom frame member 12. Also, mites and other organisms which can infect bees with various diseases, tend to collect on the bottom frame member 12. Accordingly, it is necessary to regularly clean the bottom frame member 12. This is a very inconvenient process in prior observation hives, since the honeycombs must typically be removed in order to provide access to the bottom of the chamber 44.

Referring to FIG. 6, there is illustrated an alternative embodiment of the invention, wherein the bottom frame member 12 has a removable center section 70 which extends longitudinally between the notches 15. In use, this center section 70 can be dropped beneath the bottom frame member 12 to provide access to the inner surface of the bottom frame member 12 and to the bottom of the chamber 44. The removable section 70 may be held in place by wing nuts 71 threadedly engaged with studs (not shown) depending from the bottom frame member 12, respectively along opposite sides of the center section 70.

While, in the disclosed embodiments, the observation hive 10 has been illustrated as including two honeycomb frames 50 and 55 in the chamber 44, it will be appreciated that the main frame 11 could be dimensioned to accommodate a larger number of honeycomb frames. For example, the hive could be dimensioned to accommodate two of the frames 50, stacked one above the other, and two of the frames 55 stacked above the frames 50, so that the main frame 11 is substantially twice as high as that illustrated in the drawings. Thus, the shallow honeycomb frames 55, which may be used for storage of honey by foraging bees, can easily be removed for collection of the honey, without disturbing the standard honeycomb frames 50, which may be used for breeding. It will be appreciated that other numbers of frames could also be included, by simply changing the dimensions of the side frame members 30 and the transparent walls 42 and 43.

From the foregoing, it can be seen that there has been provided an improved observation hive, which is of relatively simple and economical construction which, provides stability and improved vertical air flow for efficient moisture removal, which maintains the honeycomb frames accurately positioned in the hive, and which avoids spaces where bees can move out of the view of the observer.

While particular embodiments of the present invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

I claim:

1. An observation hive for honey bees and the like comprising: a main frame including a bottom frame member and two opposed side frame members spaced apart a predetermined lateral distance and spaced-apart front and rear top frame members, spaced-apart front and rear walls disposed within said main frame respectively against said front and rear top frame members and cooperating with said bottom and side frame members to define an open-top chamber, at least one of said walls being transparent, a removable cover overlying said side and top frame members for closing Said chamber, a honeycomb frame removably mounted in said chamber and spaced from said bottom frame member and from said cover and from said walls, each of said bottom frame member and said cover having at least one ventilation opening formed vertically therethrough and communicating with said chamber to accommodate air flow vertically through the entire vertical extent of said chamber, each of the openings having a lateral dimension substantially less than the predetermined lateral distance and being spaced from said side frame members and from said front and rear walls, support pedestals connected to said bottom frame member for establishing a clearance space therebeneath, and screens respectively covering said ventilation openings to permit passage of air and prevent passage of bees, said openings being dimensioned to afford adequate air flow to remove moisture from said chamber.

2. The observation hive of claim 1, wherein each of said bottom frame member and said cover has a plurality of ventilation openings formed therethrough.

3. The observation hive of claim 1, wherein each of said ventilation openings has a vertical extent substantially greater than the thickness of a screen and terminating at upper and lower ends, each of said openings being provided with two screens respectively at the upper and lower ends thereof.

4. The observation hive of claim 1, and further comprising a feeder carried by said main frame adjacent to said bottom frame member.

5. The observation hive of claim 4, wherein said feeder is carried by one of said pedestals outboard of the adjacent one of said side frame members.

6. The observation hive of claim 1, wherein said bottom frame member includes a removable section for facilitating access to said chamber.

7. The observation hive of claim 1, wherein each of said pedestals extends forwardly and rearwardly beyond said bottom frame member and said side frame members to inhibit forward and rearward tipping of said main frame.

8. The observation hive of claim 1, wherein said observation hive includes two honeycomb frames removably mounted in said chamber and spaced apart vertically.

9. An observation hive for honey bees and the like comprising: a main frame including a bottom frame member and two opposed side frame members and spaced-apart front and rear top frame members having substantially coplanar bottom edges, spaced-apart front and rear walls disposed within said main frame respectively against said front and rear top frame members and cooperating with said bottom and side frame members to define an open-top chamber, at least one of said walls being transparent, a removable cover overlying said side and top frame members for closing said chamber, and a honeycomb frame removably mounted in said chamber and spaced from said bottom frame member and from said cover and from said walls, said cover including an insert portion depending between said side frame members and between said top frame members and substantially completely occupying the portion of said chamber which extends above the bottom edges of said top frame members.

10. The observation hive of claim 9, wherein each of said side frame members is provided at the upper end thereof with front and rear notches, said top frame members being respectively seated in said notches.

11. The observation hive of claim 10, and further comprising reinforcing blocks respectively fixed to said side frame members at the upper ends thereof, each of said reinforcing blocks having front and rear notches aligned with the notches in said side frame members for accommodating said top frame members.

12. The observation hive of claim 11, wherein each of said reinforcing blocks includes a threaded stud projecting upwardly therefrom, said cover having openings respectively receiving said studs thereto, and further comprising wing nuts respectively threadedly engageable with said studs for retaining said cover in place.

13. The observation hive of claim 9, wherein said cover is of unitary one-piece construction.

14. The observation hive of claim 9, and further comprising shield panels respectively engageable with said main frame at the front and rear sides thereof for respectively covering said walls.

15. An observation hive for honey bees and the like comprising: a main frame including a bottom frame member and two opposed side frame members and spaced-apart front and rear top frame members, spaced-apart front and rear walls disposed within said main frame respectively against said front and rear top frame members and cooperating with said bottom and side frame members to define an open-top chamber, at least one of said walls being transparent, a removable cover overlying said side and top frame members for closing said chamber, a honeycomb frame removably mounted in said chamber and spaced from said bottom frame member and from said cover and from said walls, and spacing structure coupled to each of said side frame members and including lateral spacers extending laterally inwardly to engage said honeycomb frame at a surface thereof which is non-parallel to the direction of extent of said spacers for maintaining a predetermined minimum spacing between said honeycomb frame and said side frame members.

16. The observation hive of claim 15, wherein each of said lateral spacers comprises a stud projecting laterally.

17. The observation hive of claim 15, wherein each of said side frame members has a longitudinal channel formed on an inner surface thereof, said spacing structure including spacer blocks respectively slidably received in said channels, said honeycomb frame including a mounting member respectively carried by said spacer blocks for vertically positioning said honeycomb frame in said chamber, said lateral spacers being carried by said spacer blocks.

18. The observation hive of claim 15, wherein each of said side frame members has a longitudinal channel formed on an inner surface thereof, said honeycomb frame is a first honeycomb frame and further comprising a second honeycomb frame disposed in said chamber, said spacing structure including a first pair of spacing blocks slidably received in said channels, said first honeycomb frame including support members respectively seated on said first spacer blocks, said spacing structure including a second pair of spacer blocks slidably received in said channels on top of said support members, said second honeycomb frame including support members respectively seated on said second spacer blocks for vertically spacing said first and second honeycomb frames.

19. The observation hive of claim 18, wherein said spacing structure includes lateral spacers extending laterally from each of said spacing blocks.

* * * * *